United States Patent
Ma et al.

(10) Patent No.: US 8,710,253 B2
(45) Date of Patent: Apr. 29, 2014

(54) SOLUTION BASED PRECURSORS

(75) Inventors: Ce Ma, San Diego, CA (US); Kee-Chan Kim, Carlsbad, CA (US); Graham Anthony McFarlane, Carlsbad, CA (US)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 13/378,180

(22) PCT Filed: Jul. 1, 2010

(86) PCT No.: PCT/US2010/040765
§ 371 (c)(1),
(2), (4) Date: Mar. 5, 2012

(87) PCT Pub. No.: WO2011/005653
PCT Pub. Date: Jan. 13, 2011

(65) Prior Publication Data
US 2012/0178953 A1   Jul. 12, 2012

Related U.S. Application Data

(60) Provisional application No. 61/223,105, filed on Jul. 6, 2009.

(51) Int. Cl.
C07F 7/00 (2006.01)
C07F 17/00 (2006.01)
C23C 16/00 (2006.01)

(52) U.S. Cl.
USPC .......... 556/53; 427/248.1; 427/587; 106/1.25

(58) Field of Classification Search
USPC .................. 556/53; 427/248.1, 587; 106/1.25
See application file for complete search history.

(56) References Cited

U.S. PATENT DOCUMENTS

| | | | |
|---|---|---|---|
| 5,407,884 A | 4/1995 | Turner et al. | |
| 6,824,824 B2 * | 11/2004 | Saito | 427/255.28 |
| 6,969,539 B2 * | 11/2005 | Gordon et al. | 427/255.29 |
| 2007/0042224 A1 * | 2/2007 | Reuter et al. | 428/698 |
| 2007/0045752 A1 | 3/2007 | Forbes et al. | |
| 2008/0026578 A1 | 1/2008 | Shenai-Khatkhate et al. | |
| 2008/0176375 A1 | 7/2008 | Erben et al. | |
| 2008/0282970 A1 * | 11/2008 | Heys et al. | 117/104 |

FOREIGN PATENT DOCUMENTS

| | | |
|---|---|---|
| WO | WO 02/27063 A2 | 4/2002 |
| WO | WO 2007/140813 A1 | 12/2007 |

OTHER PUBLICATIONS

Carta et al., Surface & Coating Technology, vol. 201, No. 22-23, pp. 9289-9293 (2007).*
Kukli et al, Atomic layer deposition of ZrO2 and HfO2 on deep trenched and planar silicon, Microelectronic Engineering, 2007, vol. 84, Elsevier, pp. 2010-2013.
The corresponding Supplementary EP application search report is attached.

* cited by examiner

*Primary Examiner* — Porfirio Nazario Gonzalez
(74) *Attorney, Agent, or Firm* — David A. Hey

(57) ABSTRACT

Solution-based precursors for use as starting materials in film deposition processes, such as atomic layer deposition, chemical vapor deposition and metalorganic chemical vapor deposition. The solution-based precursors allow for the use of otherwise solid precursors that would be unsuitable for vapor phase deposition processes because of their tendency to decompose and solidify during vaporization.

13 Claims, 5 Drawing Sheets solvent BP << precursor BP solvent BP < precursor BP

SOLUTION BASED PRECURSORS

FIELD OF THE INVENTION

The present invention relates to new and useful solution-based precursors for use as starting materials in film deposition processes. The present invention particularly relates to solution-based precursors that can be used in atomic layer deposition (ALD), chemical vapor deposition (CVD) and metalorganic chemical vapor deposition (MOCVD) processes for the deposition of thin films for semiconductor devices.

BACKGROUND OF THE INVENTION

Moore's law describes a long-term trend in the history of computing hardware. In particular, since the invention of the integrated circuit in 1958, the number of transistors that can inexpensively be included in an integrated circuit has increased exponentially, doubling about every two years. This trend was first reported on by Gordon E. Moore in 1965 and has continued to the present. One view is that this scaling trend will continue for another decade. A second view is that additional functionalities will be required and that simple scaling is near an end, "more than the Moore". In either case, new materials and new device structures are emerging to meet the challenges posed by the technology and economic considerations.

The capabilities of digital electronic devices, such as processing speed, memory capacity, the number and size of pixels in digital cameras, etc, are strongly linked to Moore's law, with all such capabilities improving at roughly exponential rates as well. This increase in capability has dramatically increased the usefulness of digital electronics in nearly every segment of the world economy.

In order to continue the trend for semiconductor chip integration in accordance with either Moore's law or the "more than the Moore" viewpoint, it will be necessary to use new materials incorporated with silicon-based IC chips. These new materials will need to provide enhanced chip performance as well as help reduce unit cost.

Numerous group 2 and transition (group 3 10 12) metals have been suggested in recent years as candidates for providing critical functionalities in electronic devices. However, precursors for group 2 and transition metals are generally solid materials that are difficult to use in vapor phase deposition processes, such as ALD, CVD and MOCVD processes. In ALD processes, the requirements for precursor materials are far more stringent than the requirements for precursors used in CVD or MOCVD processes. In particular, any precursor decomposition or self-growth without a co-reactant can result in quality issues, such as higher impurity and non-uniformity in the film. Decomposition occurs at elevated temperatures for some standard amine based liquid precursors. Strong inter-molecular and intra-molecular interactions of and for some thermally stable solid precursors could result in polymerization and self-growth often occurs during the thin film growth. Furthermore, some of those solid precursor materials suffer decomposition or solidification when heated in attempts to sublimate measurable vapors for use in deposition of thin specialty films on a semiconductor wafer.

Therefore, there is a need in the art for improvements to precursors for use in vapor phase deposition processes.

SUMMARY OF THE INVENTION

The present invention provides new solution-based precursors for use in vapor phase deposition processes, such as ALD, CVD and MOCVD processes. The solution-based precursors according to the present invention do not decompose or solidify during vaporization and are therefore ideal for use in vapor phase deposition processes. If solution formulations such as those of the present invention are not used, many solid precursors by themselves can not be employed in vapor phase deposition because of decomposition or solidification in a sublimating source at elevated temperatures.

DETAILED DESCRIPTION OF THE INVENTION

Figure 1:
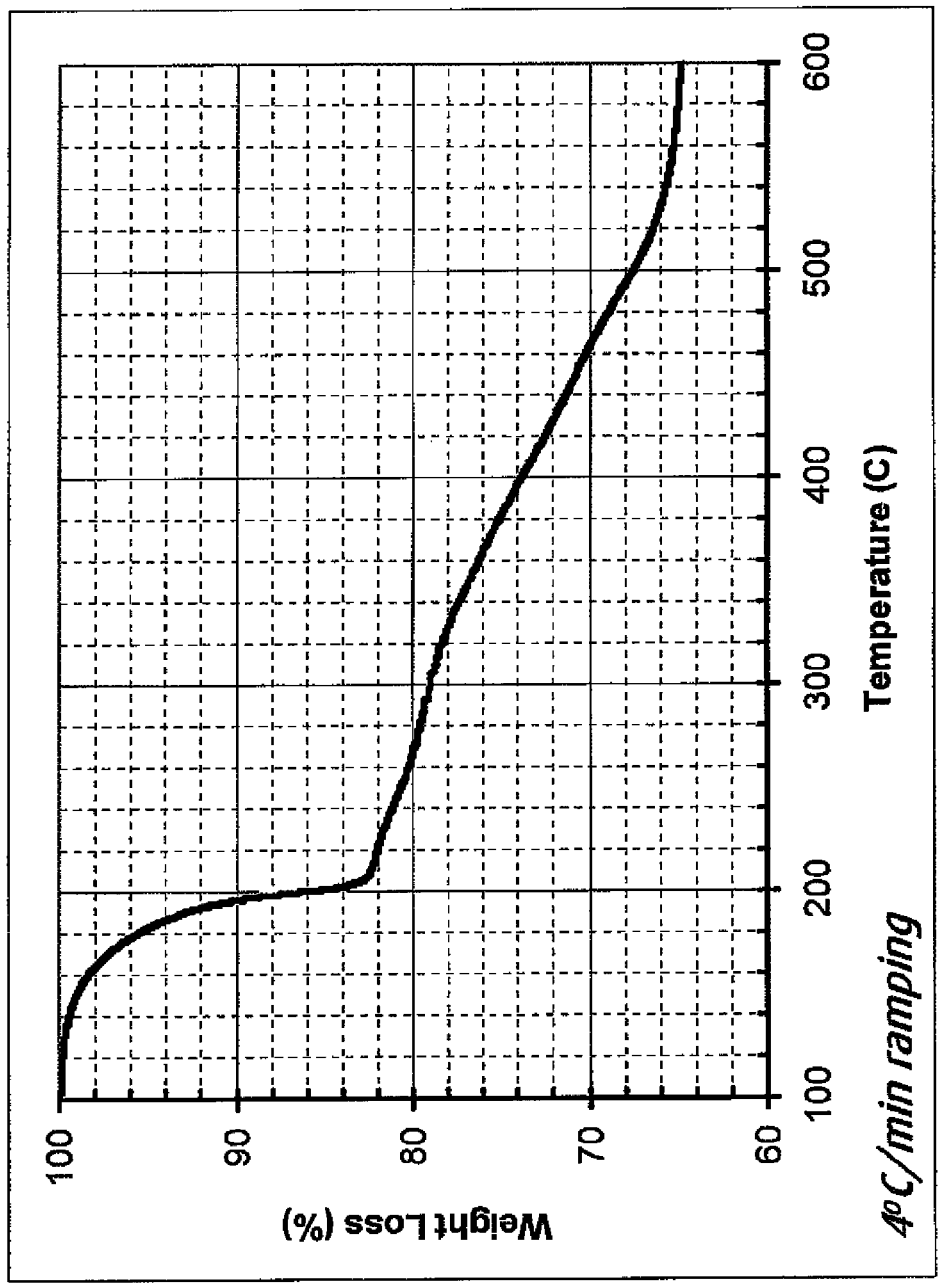
FIG. 1 is a graph showing thermogravimetric analysis results for a solid precursor material.

The present invention relates to new solution-based precursors for use in vapor phase deposition processes. A number of solid zirconium complexes were studied. In particular, $(MeCp)_2ZrMe_2$, $(Me_5Cp)_2ZrMe_2$, and $(t-BuCp)_2ZrMe_2$, wherein Me is methyl, t-Bu is t-butyl and Cp is cyclopentadienyl, were investigated. FIG. 1 is a graph showing the thermogravimetric analysis results for solid $(t-BuCp)_2ZrMe_2$. As can be seen in this graph, while there is an initial weight loss upon heating of the solid material, probably because of the gradual removal of methyl or other hydrocarbon groups, there is also a high level of residue indicating decomposition and solidification of the material. In particular, for solid $(t-BuCp)_2ZrMe_2$, the non-volatile residue remains about 65% of the initial weight. This shows that the solid form of this material would not be suitable as a precursor for vapor phase deposition processes.

In accordance with the present invention, materials that are unsuitable for vaporization in their solid form have been found to be acceptable precursor materials when first dissolved in a suitable solvent. For example, $(t-BuCp)_2ZrMe_2$ was dissolved in a purified solvent, such as n-octane, as room temperature. Solubility of the solid is greater than 0.2M and solution concentration for deposition applications such as ALD, is from 0.05M to 0.15M, preferably 0.1M. The solvent is preferably oxygen-free.

Figure 2:
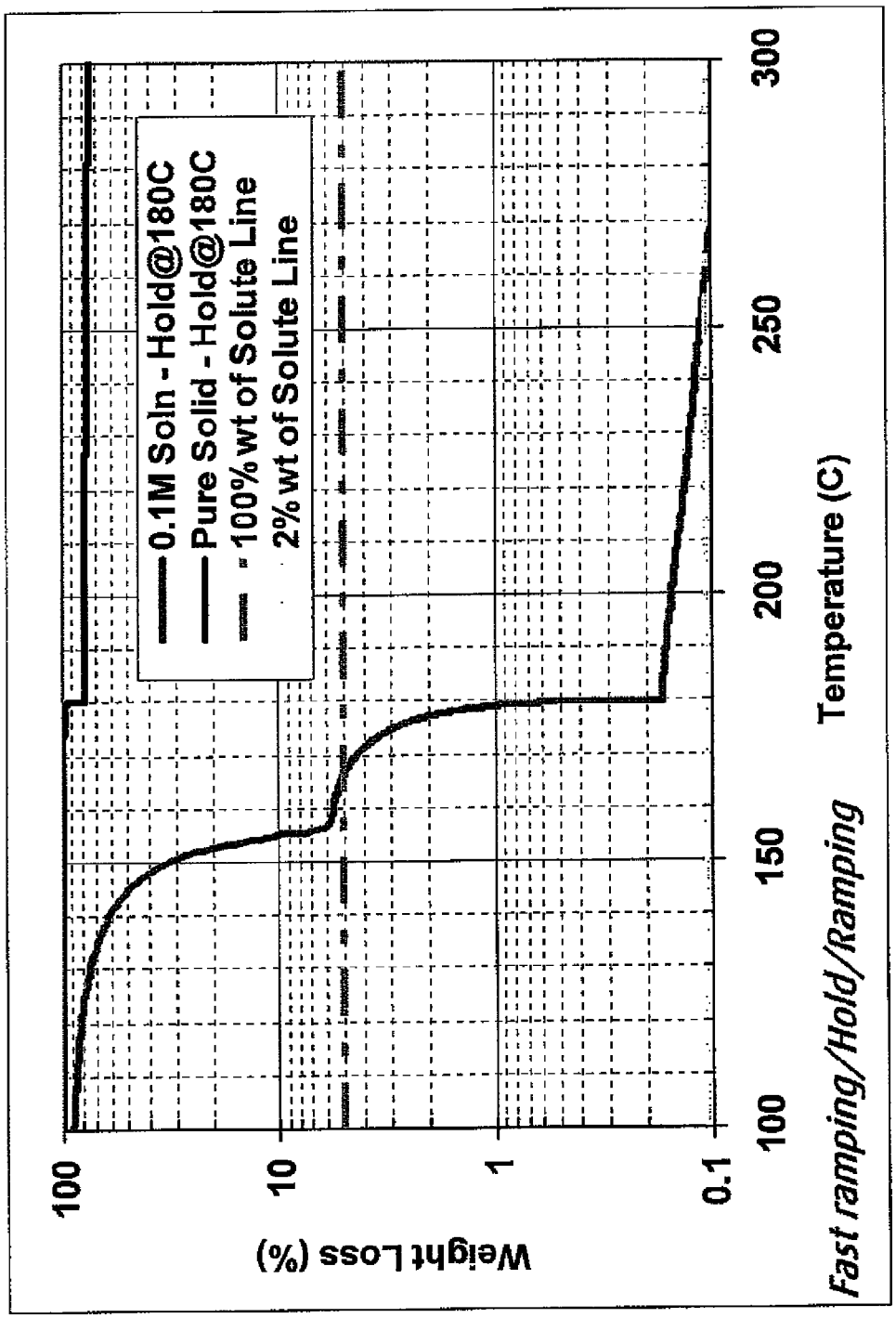
FIG. 2 is a graph showing thermogravimetric analysis results for a solution-based precursor material according to the present invention.
Figure 3A:
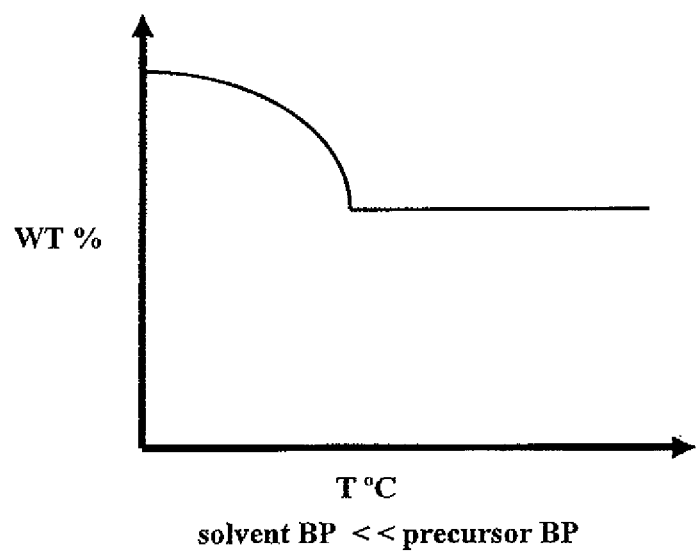
FIG. 3A-3D are graphs showing the changes in vaporization behavior dependent on the use of different solvents according to the present invention.
Figure 3B:
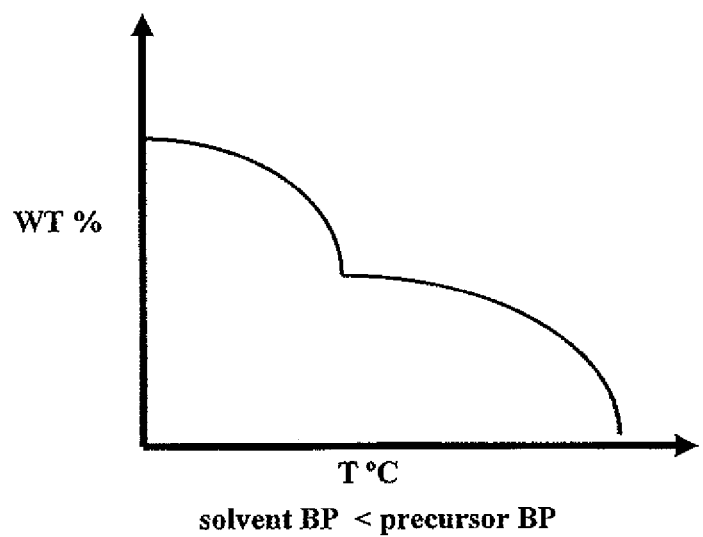
Figure 3C:
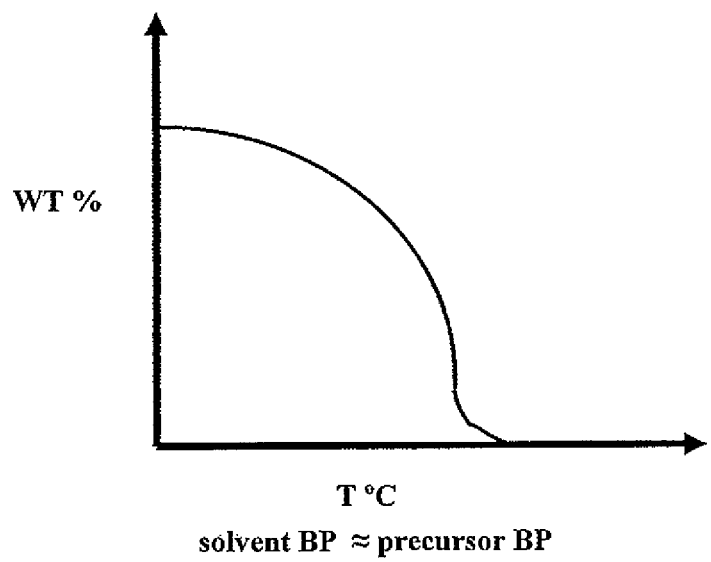
Figure 3D:
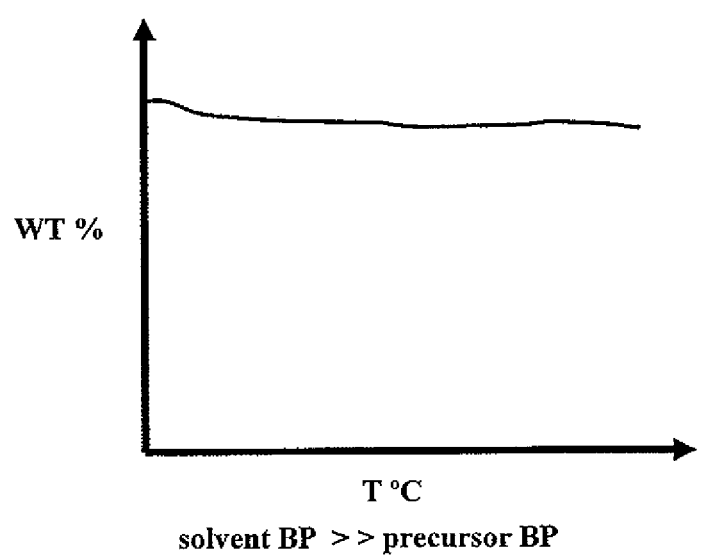

This solution was then studied by thermogravimetric analysis and the results are shown in FIG. 2. Because of the solvent effect, the dissolved precursor material is vaporized without forming solid residue, and final residue amount is less than 2% of the original solute weight. This solvent effect protects the precursor molecules in both dissolved phase and in vapor form. In the solvent rich environment, the precursor molecules are encapsulated and left together without losing methyl or other hydrocarbon groups at the vaporization temperatures. By further matching of solvent and precursor properties according to the present invention, a continuous vaporization curve can be achieved without any residue formation. FIG. 3 shows the systematic vaporization behavior changes depending on different solvents used. In particular, as solvent and precursor boiling points (as shown in FIG. 3) and other physical properties get closer to each other, a single, more uniform weight loss curve can be achieved. FIG. 3A shows that when solvent boiling point is much less than precursor boiling point, the result is an initial weight loss that reaches a minimum level, thus leaving a significant amount of precursor in non-vaporized form. FIGS. 3b and 3C show that as solvent boiling point approaches precursor boiling point, the weight loss curve becomes more singular and achieves nearly total vaporization of the precursor. FIG. 3D shows that when precursor boiling point is much higher than solvent boiling point, that almost no vaporization of the precursor occurs. Therefore, by carefully matching precursor and solvent physical properties, precursor vaporization can be optimized, although the acceptable window is relatively wide as shown by FIGS. 3B and 3C. Solvent based precursors of the present invention exhibiting these properties are suitable for any vapor phase deposition process, including ALD, CVD and MOCVD processes.

The solvent should be inert to the precursor to avoid any reaction between them during the thermal processing. Hydrocarbon based solvents, such as alkanes, alkenes, alkynes and aromatics are preferred.

Delivery of the solution-based precursors of the present invention can be carried out at room temperature using a direct liquid injection to a point of use vaporizer. The solution may then be vaporized and delivered to the deposition chamber without decomposition or solidification of the precursor. For example, for an ALD process, the hot vapor from the vaporizer is pulsed into the deposition chamber using inert gas pressure switches to achieve an ideal square wave delivery. The vaporizer can be operated at a temperature between 150° C. and 250° C., and preferably about 190° C. By matching the solvent and precursor according to the present invention, the solvent effect allows for complete vaporization of the precursor material at these temperatures with no residue left in the vaporizer. This is important in controlling the dose amount of precursor to the deposition chamber, particularly for ALD processes.

By alternatively delivering the metal precursor and an oxygen precursor, it is possible to form thin oxide film on a substrate in the deposition chamber. For example, a $ZrO_2$ film can be formed using a metal precursor such as the solution-based $(t\text{-}BuCp)_2ZrMe_2$ precursor of the present invention and an oxidant precursor, such as water vapor, ozone or another oxygen containing gas or vapor. In particular, oxidant precursors can be water vapor, $H_2O_2$, $O_2$, $O_3$, $N_2O$, NO, CO, $CO_2$, $CH_3OH$, $C_2H_5OH$, other alcohols, other acids and other oxidants. In a similar manner metal nitride films can be formed by using a metal precursor according to the present invention together with a nitrogen containing reactant such as $NH_3$, $N_2H_4$, amines, etc. Also, the metal precursors of the present invention can be used to form metal films by using hydrogen, hydrogen atoms or other reducing agents as the second precursor.

Figure 4:
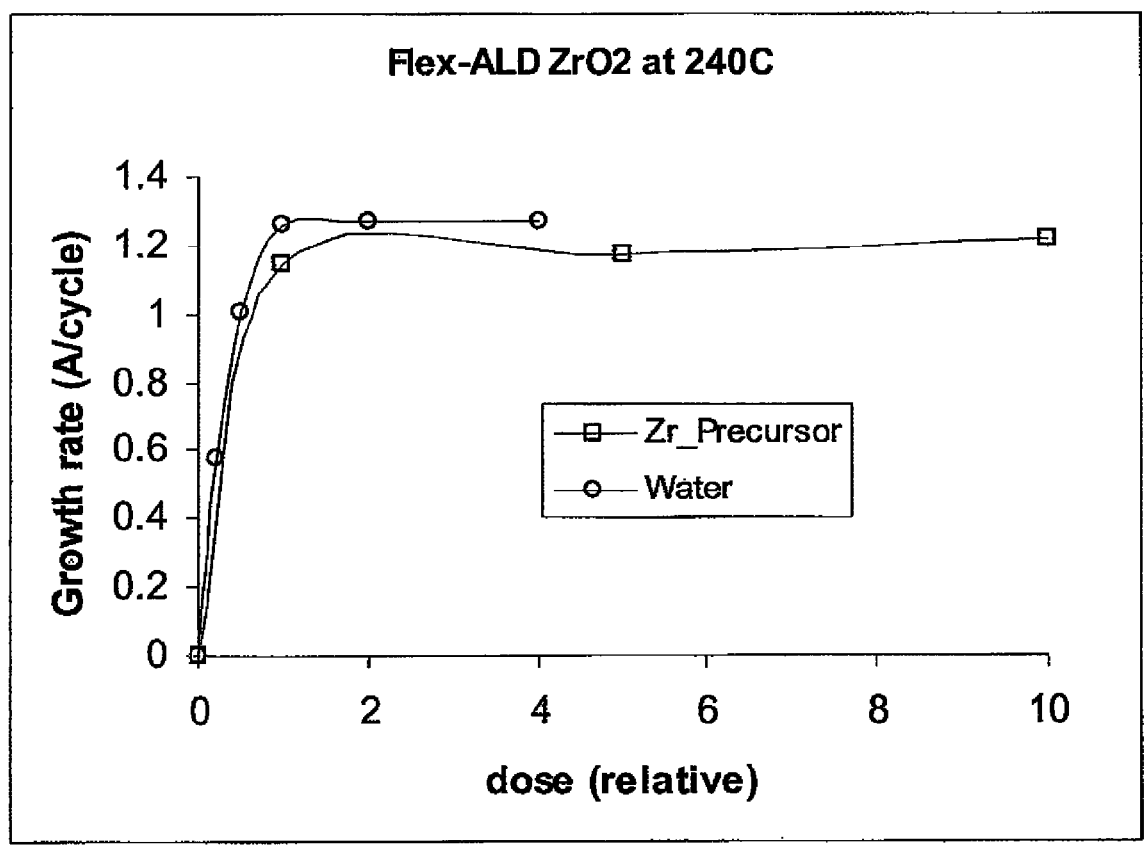
FIG. 4 is a graph showing the self-limiting growth characteristics achieved by using precursor material according to the present invention.

In one example according to the present invention, a zirconium oxide film is deposited by ALD using a $(t\text{-}BuCp)_2ZrMe_2$ precursor dissolved in n-octane and water vapor from a de-ionized water source. Saturation of growth can be observed by increasing either the Zr precursor or water dose, indicating self-limiting ALD growth, as shown in FIG. 4. No self-growth is observed when the oxidant is absent. Film growth is carried out at a temperature between 180° C. and 280° C., and preferably between 200° C. and 240° C.

The present invention provides metal-organic precursors that are dissolved in matched inert solvent. Such precursor solutions overcome the decomposition and solidification problems exhibited when using solid precursors directly, e.g. without solvents. Therefore, the solution-based precursors of the present invention represent a significant advance in the art. As discussed above, the solution-based precursors of the present invention are capable of producing high quality ALD film without self growth and solid residues. This is an improvement over the use of some oxygen containing Cp precursor that exhibit self growth. While the studies above concentrate on oxygen-free Cp precursors, the present invention is no so limited. Rather, the precursors of the present invention can have the general formula $A_xB_yM(m)$ wherein M is a metal, m is the oxidation state of the metal M and can range from 0 to 7, A and B are the same or different (where x+y=m, if m≠0 and A and B are uni-negatively charged groups; otherwise x+y=1 to 8) and can be one of the following chemical classes: (1) cyclopentadienyl (Cp) and its derivatives (R1R2R3R4R5Cp; wherein R1, R2, R3, R4 and R5 are the same or different and can be hydrogen or alkyl [$C_nH_{2n+1}$, n=1-6]); (2) primary, secondary or tertiary alkyl groups ($C_nH_{2n+1}$, n=1-12); (3) cycloalkyl groups ($C_nR_{2n-1}$, n=3-12, wherein R is hydrogen or alkyl groups); (4) cycloalkyldienes ($C_nR_{2n-4}$, n=4-12, wherein R is hydrogen or alkyl groups); (5) benzene and its derivatives (R1R2R3R4R5R6$C_6$; wherein R1, R2, R3, R4, R5 and R6 are the same or different and can be hydrogen or alkyl [$C_nH_{2n+1}$, n=1-6]); (6) amides (R1R2N, wherein R1 and R2 are the same or different and can be hydrogen or alkyl [$C_nH_{2n+1}$, n=1-6]); or (7) bidentate ligands (R1E1=C(R3)–[C(R4)=C(R5)]$_n$–E2R2; wherein E1 and E2 are the same or different and can be nitrogen, oxygen, phosphorus or sulfur; n=0-4; R1, R2, R3, R4 and R5 are the same or different and can be none, hydrogen, any alkyl or any aryl groups). Suitable solvents for the solid precursors according to the present invention have closely matched boiling points and can be alkanes, alkenes, alkynes, or aromatics. As noted above, the concentration of the solution precursors of the present invention is from 0.05M to 1.0M, preferably 0.1M.

The present invention makes it possible to use metal-organic precursor materials that can leave more than 5% solid residue, which could not previously have been used in vapor phase deposition processes because of the risk of decomposition and solidification. By using the precursors according to the solution-based chemistry of the present invention, it is possible to eliminate self-growth tendencies that have been observed when using neat metal-organic precursors.

The precursors of the present invention are useful for several applications. In particular, the precursors of the present invention may be used for forming high-k gate dielectric layers for Si, Ge, and C based group IV elemental semiconductors or for forming high-k gate dielectric layers for InGaAs, AlGaAs and other III-V high electron mobility semiconductors. In addition, the precursors of the present invention are useful for forming high-k capacitors for DRAM, flash, phase-change and resistive memory devices. The precursors of the present invention can also be used as metal-based catalysts for gas purification, organic synthesis, fuel cell membranes and chemical detectors, or as metal-based surfaces for electrode materials in fuel cells.

It will be understood that the embodiments described herein are merely exemplary and that one skilled in the art may make variations and modifications without departing from the spirit and scope of the present invention. All such variations and modifications are intended to be included within the scope of the invention as described above. Further, all embodiments disclosed are not necessarily in the alternative, as various embodiments of the invention may be combined to provide the desired result.

What is claimed is:

1. A solution-based precursor comprising a solid precursor dissolved in a solvent having a boiling point closely matched to that of the solid precursor, the precursor having the formula:

$$A_xB_yM(m)$$

wherein M is a metal, m is the oxidation state of the metal M and is from 0 to 7, and A and B are the same or different and are selected from the group of chemical classes comprising a) cyclopentadienyl (Cp) and its derivatives (R1R2R3R4R5Cp; wherein R1, R2, R3, R4 and R5 are the same or different and can be hydrogen or alkyl [$C_nH_{2n+1}$, n=1-6]); b) primary, secondary or tertiary alkyl groups ($C_nH_{2n+1}$, n=1-12); c) cycloalkyl groups ($C_nR_{2n-1}$, n=3-12, wherein R is hydrogen or alkyl groups); d) cycloalkyldienes ($C_nR_{2n-4}$, n=4-12, wherein R is hydrogen or alkyl groups); e) benzene and its derivatives (R1R2R3R4R5R6$C_6$; wherein R1, R2, R3, R4, R5 and R6 are the same or different and can be hydrogen or alkyl [$C_nH_{2n+1}$, n=1-6]); f) amides (R1R2N, wherein R1 and R2 are the same or different and can be hydrogen or alkyl [$C_nH_{2n+1}$, n=1-6]); and g) bidentate ligands (R1E1=C(R3)–[C(R4)=C(R5)]$_n$–E2R2, wherein E1 and E2 are the same or different and can be nitrogen, oxygen, phosphorus or sulfur, n=0-4, R1, R2, R3, R4 and R5 are the same or different and can be none, hydrogen, any alkyl or any aryl groups) and wherein x+y=m, if m≠0 and A and B are uni-negatively charged groups or otherwise x+y=1 to 8.

2. A precursor according to claim 1 comprising (MeCp)$_2$ZrMe$_2$, (Me$_5$Cp)$_2$ZrMe$_2$, or (t-BuCp)$_2$ZrMe$_2$, wherein Me is methyl, t-Bu is t-butyl and Cp is cyclopentadienyl.

3. A precursor according to claim 1 wherein the solvent is an alkane, alkene, alkyne, or aromatic.

4. A precursor according to claim 1 wherein the concentration of the solution is 0.05M to 1.0M.

5. A precursor according to claim 4 wherein the concentration is 0.1M.

6. A method of forming a thin oxide film comprising alternately delivering a solution-based metal precursor and an oxygen precursor to a substrate in the deposition chamber, wherein the metal precursor is a solid precursor dissolved in a solvent having a boiling point closely matched to that of the solid precursor and the metal precursor has the formula:

$$A_xB_yM(m)$$

wherein M is a metal, m is the oxidation state of the metal M and is from 0 to 7, and A and B are the same or different and are selected from the group of chemical classes comprising a) cyclopentadienyl (Cp) and its derivatives (R1R2R3R4R5Cp; wherein R1, R2, R3, R4 and R5 are the same or different and can be hydrogen or alkyl [$C_nH_{2n+1}$, n=1-6]); b) primary, secondary or tertiary alkyl groups ($C_nH_{2n+1}$, n=1-12); c) cycloalkyl groups ($C_nR_{2n-1}$, n=3-12, wherein R is hydrogen or alkyl groups); d) cycloalkyldienes ($C_nR_{2n-4}$, n=4-12, wherein R is hydrogen or alkyl groups); e) benzene and its derivatives (R1R2R3R4R5R6$C_6$; wherein R1, R2, R3, R4, R5 and R6 are the same or different and can be hydrogen or alkyl [$C_nH_{2n+1}$, n=1-6]); f) amides (R1R2N, wherein R1 and R2 are the same or different and can be hydrogen or alkyl [$C_nH_{2n+1}$, n=1-6]); and g) bidentate ligands (R1E1=C(R3)–[C(R4)=C(R5)]$_n$-E2R2, wherein E1 and E2 are the same or different and can be nitrogen, oxygen, phosphorus or sulfur, n=0-4, R1, R2, R3, R4 and R5 are the same or different and can be none, hydrogen, any alkyl or any aryl groups) and wherein x+y=m, if m≠0 and A and B are uni-negatively charged groups or otherwise x+y=1 to 8.

7. A method according to claim 6 wherein the solvent is an alkane, alkene, alkyne, or aromatic.

8. A method according to claim 6 wherein the oxygen precursor is water vapor, $H_2O_2$, $O_2$, $O_3$, $N_2O$, NO, CO, $CO_2$, $CH_3OH$, $C_2H_5OH$, other alcohols, other acids or another oxidant.

9. A method according to claim 6 wherein the thin film is ZrO$_2$, and the metal precursor is (t-BuCp)$_2$ZrMe$_2$ wherein Me is methyl, t-Bu is t-butyl and Cp is cyclopentadienyl.

10. A method of forming a thin nitride film comprising alternately delivering a solution-based metal precursor and a nitrogen precursor to a substrate in the deposition chamber, wherein the metal precursor is a solid precursor dissolved in a solvent having a boiling point closely matched to that of the solid precursor and the metal precursor has the formula:

$$A_xB_yM(m)$$

wherein M is a metal, m is the oxidation state of the metal M and is from 0 to 7, and A and B are the same or different and are selected from the group of chemical classes comprising a) cyclopentadienyl (Cp) and its derivatives (R1R2R3R4R5Cp; wherein R1, R2, R3, R4 and R5 are the same or different and can be hydrogen or alkyl [$C_nH_{2n+1}$, n=1-6]); b) primary, secondary or tertiary alkyl groups ($C_nH_{2n+1}$, n=1-12); c) cycloalkyl groups ($C_nR_{2n-1}$, n=3-12, wherein R is hydrogen or alkyl groups); d) cycloalkyldienes ($C_nR_{2n-4}$, n=4-12, wherein R is hydrogen or alkyl groups); e) benzene and its derivatives (R1R2R3R4R5R6$C_6$; wherein R1, R2, R3, R4, R5 and R6 are the same or different and can be hydrogen or alkyl [$C_nH_{2n+1}$, n=1-6]); f) amides (R1R2N, wherein R1 and R2 are the same or different and can be hydrogen or alkyl [$C_nH_{2n+1}$, n=1-6]); and g) bidentate ligands (R1E1=C(R3)–[C(R4)=C(R5)]$_n$–E2R2, wherein E1 and E2 are the same or different and can be nitrogen, oxygen, phosphorus or sulfur, n=0-4, R1, R2, R3, R4 and R5 are the same or different and can be none, hydrogen, any alkyl or any aryl groups) and wherein x+y=m, if m≠0 and A and B are uni-negatively charged groups or otherwise x+y=1 to 8.

11. A method according to claim 10 wherein the solvent is an alkane, alkene, alkyne, or aromatic.

12. A method according to claim 10 wherein the nitrogen precursor is $NH_3$, $N_2H_4$, or an amine.

13. A thin film formed from a solution based metal precursor wherein the metal precursor is a solid precursor dissolved in a solvent having a boiling point closely matched to that of the solid precursor and the metal precursor has the formula:

$$A_xB_yM(m)$$

wherein M is a metal, m is the oxidation state of the metal M and is from 0 to 7, and A and B are the same or different and are selected from the group of chemical classes comprising a) cyclopentadienyl (Cp) and its derivatives (R1R2R3R4R5Cp; wherein R1, R2, R3, R4 and R5 are the same or different and can be hydrogen or alkyl [$C_nH_{2n+1}$, n=1-6]); b) primary, secondary or tertiary alkyl groups ($C_nH_{2n+1}$, n=1-12); c) cycloalkyl groups ($C_nR_{2n-1}$, n=3-12, wherein R is hydrogen or alkyl groups); d) cycloalkyldienes ($C_nR_{2n-4}$, n=4-12, wherein R is hydrogen or alkyl groups); e) benzene and its derivatives (R1R2R3R4R5R6$C_6$; wherein R1, R2, R3, R4, R5 and R6 are the same or different and can be hydrogen or alkyl [$C_nH_{2n+1}$, n=1-6]); f) amides (R1R2N, wherein R1 and R2 are the same or different and can be hydrogen or alkyl [$C_nH_{2n+1}$, n=1-6]); and g) bidentate ligands (R1E1=C(R3)–[C(R4)=C(R5)]$_n$–E2R2, wherein E1 and E2 are the same or different and can be nitrogen, oxygen, phosphorus or sulfur, n=0-4, R1, R2, R3, R4 and R5 are the same or different and can be none, hydrogen, any alkyl or any aryl groups) and wherein x+y=m, if m≠0 and A and B are uni-negatively charged groups or otherwise x+y=1 to 8.

* * * * *